United States Patent
Burke et al.

(10) Patent No.: US 10,208,001 B2
(45) Date of Patent: Feb. 19, 2019

(54) PROCESS FOR PREPARING 1,4-DIBENZODIAZEPINES VIA BUCHWALD-HARTWIG CHEMISTRY

(71) Applicant: UNIVERSIDADE DE EVORA, Evora (PT)

(72) Inventors: Anthony Burke, Evora (PT); Daniela Alexandra Silva Peixoto, Fafe (PT)

(73) Assignee: UNIVERSIDADE DE EVORA, Evora (PT)

( * ) Notice: Subject to any disclaimer, the term of this patent is extended or adjusted under 35 U.S.C. 154(b) by 0 days.

(21) Appl. No.: 15/565,589

(22) PCT Filed: Jun. 21, 2016

(86) PCT No.: PCT/IB2016/053685
§ 371 (c)(1),
(2) Date: Oct. 10, 2017

(87) PCT Pub. No.: WO2016/207790
PCT Pub. Date: Dec. 29, 2016

(65) Prior Publication Data
US 2018/0105502 A1 Apr. 19, 2018

(30) Foreign Application Priority Data

Jun. 22, 2015 (PT) .......................... 108566

(51) Int. Cl.
C07D 243/38 (2006.01)
C07D 243/10 (2006.01)
B01J 31/24 (2006.01)

(52) U.S. Cl.
CPC ............ *C07D 243/10* (2013.01); *B01J 31/24* (2013.01)

(58) Field of Classification Search
CPC .................................................. C07D 243/38
USPC ....................................................... 540/557
See application file for complete search history.

(56) References Cited

PUBLICATIONS

D. Tsvelikhovsky, et al; Concise palladium-catalyzed synthesis of dibenzodiazepines and structural analogues; Journal of the American Chemical Society; XP-002761120; vol. 133; Aug. 2011; pp. 14228-14231.
S. Fang, et al; A one-pot synthetic strategy for construction of the dibenzodiazepnie skeleton via a transition metal-free process; Organic & Biomolecular Chemistry; XP-002761121; vol. 12; Jul. 2013; pp. 6895-6900.
I.R. Siddiqui, et al; MoO2Cl2(DMF)2 catalyzed microwave assisted reductive cyclisation of nitroaromatics into . . . ; RSC Advances; XP-002761122; vol. 5; Dec. 2014; pp. 5256-5260.
X. Li, et al; Construction of 1,4-Benzodiazepine skeleton from 2-(Arylamino)benzamides through . . . ; The Journal of Organic Chemistry; XP-002761123; vol. 79; Jan. 2014; pp. 955-962.
International Search Report dated Sep. 9, 2016 for PCT/IB2016/053685.
Written Opinion dated Sep. 9, 2016 for PCT/IB2016/053685.

*Primary Examiner* — Brenda L Coleman
(74) *Attorney, Agent, or Firm* — Lucas & Mercanti, LLP

(57) ABSTRACT

The present application provides a one-pot catalytic process which involves the formation of 1,4-dibenzodiazepines from o-haloaldimines (either pre-formed or formed in situ) of formula (I) and o-haloanilines of formula (II) via a palladium catalyzed Buchwald-Hartwig reaction and a cyclization sequence, to afford the 1,4-dibenzodiazepine products of formula (III). The present application describes the preparation of the 1,4-dibenzodiazepine products of formula (III) from simple commercial raw materials by efficient processes.

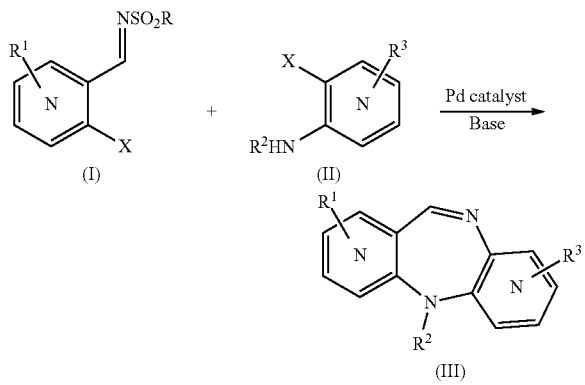

10 Claims, No Drawings

PROCESS FOR PREPARING 1,4-DIBENZODIAZEPINES VIA BUCHWALD-HARTWIG CHEMISTRY

CROSS REFERENCE TO RELATED APPLICATION

This Application is a 371 of PCT/IB2016/053685 filed on Jun. 21, 2016, which claims priority of Portuguese Application No. 108566 filed Jun. 22, 2015, both of which are incorporated herein by reference.

TECHNICAL FIELD

The present application refers to a catalytic process to afford 1,4-dibenzodiazepines from o-haloaldimines and o-haloanilines via a palladium catalyzed Buchwald-Hartwig reaction and what appears to be an unusual cyclization sequence.

BACKGROUND

Pharmaceuticals bearing the 1,4-dibenzodiazepine core are a very important class of drugs. The first reported synthesis of a dibenzodiazepine (dibenzooxazepine) was clozapine and loxapine (Hunziker et al. 1964). Since this time other routes have been developed that rely on accessing them from their amide, lactam or other precursors (Lednicer 1998 and Tsvelikhovsky and Buchwald, 2011). Some important analogues with attractive medicinal properties, include the dibenzodiazepinones, sintamil for treating depression, diazepinomicin an antimicrobial alkaloid (Charan et al. 2004) and pirenzapine, an M1 selective antagonist (antimuscarinic agent), used in the treatment of peptic ulcers (Yazdanian et al. 1998). Five synthetic approaches have been developed to access dibenzodiazepinones (Li et al. 2014, one of the methods was retracted in 2014—Diao et al. 2011). Not many methods have recently been described for accessing dibenzooxazepins. The method of Buchwald and Tsvelikhovsky is particularly of note (Tsvelikhovsky and Buchwald, 2011). This method involves a Buchwald-Hartwig amination (Guram et al. 1995, Hartwig 2000, Louie and Hartwig 1995, Burke and Marques, 2015) to form the key diarylamine intermediate, followed by a Pd-catalyzed ammonia cross-coupling that terminates with a ketone condensation (Scheme 1). The reaction requires the use of 5-7 equivalents of ammonia, and the yields ranged from 43-93% for 9 examples. Only the tBu-DavePhos ligands provided satisfactory results, and it was suggested that the dimethylamino group present in the flanking ring is key to obtaining the desired reactivity (Lundgren and Stradiotto, 2012). This method constituted the first application of the Pd-Catalyzed coupling of ammonia in the synthesis of complex heterocycles. However, the reaction was carried out in two independent steps, requiring first the preparation of the diarylamine, followed by amination with ammonia and cyclization, as illustrated in the following scheme 1.

Scheme 1

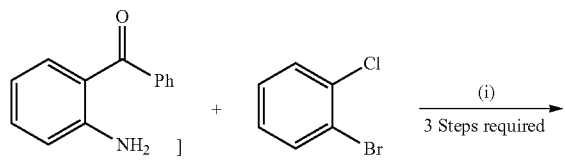

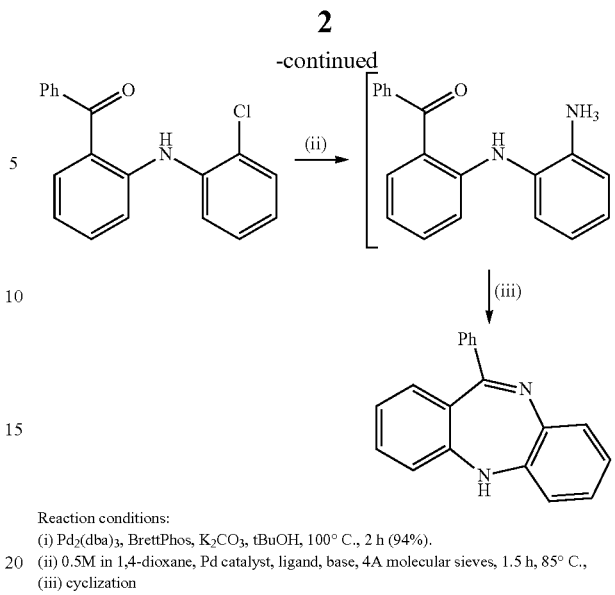

Reaction conditions:
(i) Pd$_2$(dba)$_3$, BrettPhos, K$_2$CO$_3$, tBuOH, 100° C., 2 h (94%).
(ii) 0.5M in 1,4-dioxane, Pd catalyst, ligand, base, 4A molecular sieves, 1.5 h, 85° C.,
(iii) cyclization Thus, the present invention intends to provide a new efficient catalytic process which affords dibenzooxazepines in good yields.

SUMMARY

It is the goal of this application to report the development of the formation of 1,4-dibenzodiazepines from o-haloaldimines (either pre-formed or formed in situ) of formula (I) and o-haloanilines of formula (II) via a palladium catalyzed Buchwald-Hartwig reaction and a cyclization sequence, to afford the 1,4-dibenzodiazepine products of formula (III).

The reaction yields are good, and the process is overall very sustainable and atom-economical, its principle advantage is its inherent capacity for product structural diversity generation, and thus has immense potential for preparing multiple-libraries of interesting and useful biologically active molecules.

The imine substrates used in the process are prepared (or generated in situ) from simple commercial raw materials by efficient processes, some of which are catalytic themselves. The cyclization reactions can be run at temperatures of between 50° C. and 130° C. using a variety of catalysts. These reactions are Pd catalyzed, the union of the metal complex with the ligand—generally a phosphane like, PPh$_3$, SPhos, XPhos or XantPhos, etc) forms the active catalyst which interacts with the substrate.

Loadings of between 0.1 and 5 mol % of the metal complex can be used. The mechanism is not known for sure, but there are strong indications that there is first a Buchwald-Hartwig coupling reaction between the imine and the o-haloaniline to give a diarylaminoimine that undergoes a hitherto unknown N-arylation with expulsion of the arylsulfonyl unit prior or after this ring-closure event (Peixoto et al. 2015).

In this context, the present application describes a novel process for the catalytic synthesis of 1,4-dibenzodiazepines from simple precursors, in other words, the substrates of formula (I) and formula (II) react under catalytic conditions to give products of formula (III) comprising the use of a suitable metal catalyst, wherein the reaction is conducted by adding the palladium pre-catalyst from an appropriate metal complex like, Pd(OAc)$_2$, PEPPSI-iPr, PdCl$_2$(dppf), Pd(PPh$_3$)$_4$ in the presence of a base.

In an embodiment, the preformed catalyst is prepared by adding the ligand to the metal complex in a suitable dry solvent, under an inert atmosphere and allowing the mixture to stir up to 24 h, in a temperature range from 50 to 130° C.

In another embodiment, the pre-catalyst used is selected from the group comprising Pd based metal complexes.

In another embodiment, the reaction solvent used is selected from the group comprising: THF, toluene, benzene, dimethyl ether, 1,4-dioxane, dichloromethane, acetonitrile, chloroform, DMF, DMA and NMP.

In yet another embodiment, the ligand used is selected from the group comprising monophosphane type ligands, like; triphenylphosphane, CyJohnPhos, SPhos, RuPhos, PCy$_3$, P(nBu)$_3$ and P(t-Bu)$_3$.

The ligand loading ranges from within 0.25 to 10 mol %.

In another embodiment, the reactions are run under an inert atmosphere (e.g. under dry nitrogen or argon).

In yet another embodiment, the reaction temperature ranges between 50° and 130° C.

GENERAL DESCRIPTION

The present application provides a catalytic process that involves o-haloaldimines and o-haloanilines that gives 1,4-dibenzodiazepines under palladium catalysis.

The substrates can be described by the formulae (I) and (II),

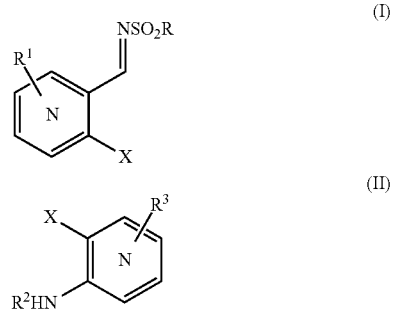

in which

X represents a halogen like, Br, Cl, I, or a triflate group (OTf),

R represents, an alkyl or aryl group,

R$^1$ and R$^3$ represent a hydrogen, a saturated alkyl, allyl, vinyl or cycloalkyl group, or an aryl group, or an OH, tiol, amino, nitro, cyano, aldehyde, ketone, ester, thioester, carboxylic acid, carbamate, ether or a thioeter group, R$^2$ represents a hydrogen, an alkyl, allyl, vinyl or aryl group, the N in both the formulae (I) and (II), can vary position between 3 and 6 in (I), considering position-1 to be the carbon attached to the imino group and 3 and 6 in (I), considering position-1 to be the carbon attached to the imino group, and between 3 and 6 in (II), considering position-1 to be the carbon attached to the amino group 6 in (II).

The sulfonylimine substrates of formula (I) are obtained from the corresponding aldehydes (Weinreb, 1997) using common literature methods. Bromide, chloride or iodide precursors can be used, with a preference for the cheaper bromides. Substrates of formula (II) are commercially available.

The reactions are normally conducted by simply adding the pre-catalyst and ligand the sulfonylimine substrates of formula (I) and the anilines of formula (II) to a flask under an inert gas atmosphere in the presence of a base like; triethylamine, K$_2$CO$_3$, Na$_2$CO$_3$, CaCO$_3$, Ba(OH)$_2$, KOAc, DIPA, K$_3$PO$_4$, NMM, DBU, KOH, KF, Cs$_2$CO$_3$, and KOtBu.

The quantity of base used ranged from 1 to 5 equivalents.

With regard to the ligands used, these were generally commercial monophosphanes, (like; triphenylphosphane, CyJohnPhos, SPhos, RuPhos, PCy$_3$, P(nBu)$_3$ and P(t-Bu)$_3$.

The ligand loading ranges from within 0.25 to 10 mol %.

The palladium complexes that were used were generally: Pd(OAc)$_2$, PEPPSI-iPr catalyst, Pd$_2$(dba)$_3$.CHCl$_3$, [Pd(TFA)$_2$], PdCl$_2$(dppf), Pd(PPh$_3$)$_4$, cationic palladium (II) complexes and Pd—NHCs.

The following reaction solvents can be used: toluene, dimethyl ether, diethyl ether, 1,4-dioxane, dichloromethane, acetonitrile, chloroform, DMF, DMA and NMP.

The reactions were run under an inert atmosphere (e.g. under dry nitrogen or argon).

For the aforementioned catalytic reaction, 0.1-5 mol % of the metal-complex is required relative to the substrate.

The reactions are generally run at temperatures of between 50° C. and 130° C. using a variety of chiral catalysts or non-chiral catalysts. Yields of up to 85% can be achieved. The reaction times varied from between 15 and 24 hours.

EXAMPLES

General Catalytic Procedure for the Synthesis of Dibenzodiazepines

The reactions were performed under a nitrogen atmosphere using a Radleys® 12 position carousel reactor station. Pd(OAc)$_2$ (2.5 mol %), SPhos (5.0 mol %), o-bromoarylimines, o-bromoarylamines, Cs$_2$CO$_3$ (2 equivs) and THF were added to the reaction tube. The reactions were performed at 100° C. for 18 h. The reactions were monitored by TLC, to follow the disappearance of the starting materials. After completion, the mixture was allowed to cool to room temperature. The reaction mixture was filtered with celite and the solvent removed under reduced pressure and then purified by column chromatography using 9:1 Hexane/EtOAc, to give the following pure compounds 1-11.

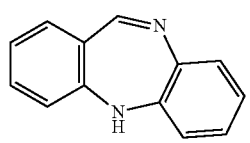

Compound 1

5H-Dibenzo[b,e][1,4]diazepine): From N-(2-bromobenzylidene)-4-methylbenzenesulfonamide (0.50 g, 1.5 mmol) and 2-bromoaniline (0.258 g), according to the general procedure, the title compound was obtained as a yellow solid (0.20 g, 70%) m.p. 124.0-124.5° C. $^1$H NMR (400 MHz, CDCl$_3$): δ 7.06-7.12 (m, 2H, ArH), 7.33-7.37 (m, 2H, ArH), 7.42-7.46 (m, 1H, ArH), 7.62-7.66 (m, 2H, ArH), 8.33 (dd, J=6.6 and 2.0 Hz, 1H, ArH), 8.76 (br s, 1H, HC=N) ppm. $^{13}$C NMR (100 MHz, CDCl$_3$): δ 118.5 (C), 120.0 (CH), 126.3 (C), 127.2 (CH), 128.0 (CH), 128.5 (CH), 129.7 (CH), 133.0 (CH), 133.2 (CH), 133.4 (CH), 134.4 (C), 150.5 (C), 160.8 (HC=N) ppm. MS (ESI− TOF) m/z: 195.2 (M$^+$+H).

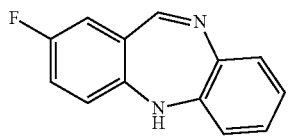

Compound 2

2-Fluoro-5H-dibenzo[b,e][1,4]diazepine: From N-(2-bromo-5-fluorobenzylidene)-4-methylbenzenesulfonamide (0.50 g, 1.3 mmol) and 2-bromoaniline (0.224 g), according to the general procedure, the title compound was obtained as a yellow solid (0.40 g, 76%) m.p. 107.2-108.8° C. $^1$H NMR (400 MHz, CDCl$_3$): δ 7.05-7.14 (m, 3H, ArH), 7.34-7.38 (m, 1H, ArH), 7.58-7.67 (m, 2H, ArH), 8.03-8.06 (m, 1H, ArH), 8.70 (br s, 1H, HC=N) ppm. $^{13}$C NMR (100 MHz, CDCl$_3$): δ 116.0 (d, J=24 Hz, CH), 118.7 (C), 119.8 (CH), 120.2 (d, J=23 Hz, CH), 127.6 (CH), 128.6 (CH), 133.3 (CH), 134.6 (d, J=7.5 Hz, CH), 136.3 (C), 146.1 (C), 150.0 (C), 159.6 (HC=N), 162.3 (d, J=239.7 Hz, C—F) ppm. MS (ESI-TOF) m/z: 213.21 (M$^+$+H).

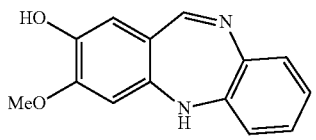

Compound 5

3-Methoxy-5H-dibenzo[b,e][1,4]diazepin-2-ol: From N-(2-bromo-5-hydroxy-4-methoxybenzylidene)-4-methylbenzenesulfonamide (0.50 g, 1.3 mmol) and 2-bromoaniline (0.224 g), according to the general procedure the title compound was obtained as a colorless oil (0.225 g, 72%). $^1$H NMR (400 MHz, CDCl$_3$): δ 3.96 (s, 3H, OMe), 4.06 (br s, 1H, OH), 5.68 (br s, 1H, NH), 7.03-7.09 (m, 3H, ArH), 7.31-7.35 (m, 1H, ArH), 7.62-7.64 (m, 1H, ArH), 7.91 (s, 1H, ArH), 8.62 (br s, 1H, HC=N) ppm. $^{13}$C NMR (100 MHz, CDCl$_3$): δ 56.5 (OMe), 114.5 (CH), 114.9 (CH), 120.0 (CH), 127.0 (CH), 128.5 (CH), 132.7 (C), 133.3 (CH), 144.2 (C), 145.5 (C), 150.3 (C), 150.6 (C), 151.8 (C), 160.1 (HC=N) ppm. MS (ESI- TOF) m/z: 241.27 (M$^+$+H).

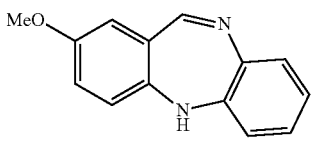

Compound 3

2-Methoxy-5H-dibenzo[b,e][1,4]diazepine: From N-(2-bromo-5-methoxybenzylidene)-4-methylbenzenesulfonamide (0.50 g, 1.4 mmol) and 2-bromoaniline (0.241 g), according to the general procedure the title compound was obtained as a brown semi-solid (0.222 g, 76%). $^1$H NMR (400 MHz, CDCl$_3$): δ 3.87 (s, 3H, OMe), 6.91-6.94 (m, 1H, ArH), 7.04-7.10 (m, 2H, ArH), 7.31-7.35 (m, 1H, ArH), 7.47-7.49 (m, 1H, ArH), 7.62-7.64 (m, 1H, ArH), 7.84-7.85 (m, 1H, ArH), 8.69 (br s, 1H, HC=N) ppm. $^{13}$C NMR (100 MHz, CDCl$_3$): δ 55.8 (OMe), 118.0 (CH), 119.9 (CH), 120.7 (CH), 127.2 (CH), 128.4 (C), 128.5 (CH), 132.6 (C), 133.1 (CH), 133.9 (CH), 134.0 (C), 134.8 (C), 150.2 (C), 160.6 (HC=N) ppm. MS (ESI- TOF) m/z: 225.27 (M$^+$+H).

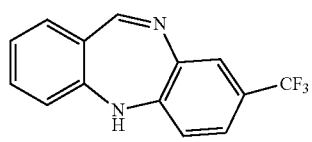

Compound 6

8-(Trifluoromethyl)-5H-dibenzo[b,e][1,4]diazepine: From N-(2-bromobenzylidene)-4-methylbenzenesulfonamide (0.50 g, 1.5 mmol) and 2-bromo-4-(trifluoromethyl)aniline (0.360 g), according to the general procedure the title compound was obtained as a yellow semi-solid (0.178 g, 46%). $^1$H NMR (400 MHz, CDCl$_3$): δ 7.10-7.12 (m, 1H, ArH), 7.37-7.46 (m, 2H, ArH), 7.59-7.67 (m, 2H, ArH), 7.90 (br s, 1H, ArH), 8.30-8.33 (m, 1H, ArH), 8.62 (br s, 1H, HC=N) ppm. $^{13}$C NMR (100 MHz, CDCl$_3$): δ 125.7 (q, J=7.0 Hz, CH), 126.6 (CH), 127.3 (CH), 129.7 (q, J=260.0 Hz, CF$_3$), 129.2 (C), 130.0 (q, J=3.8 Hz, CH), 130.3 (q, J=6.8 Hz, CH), 132.1 (q, J=30.0 Hz, C—CF$_3$), 133.7 (CH), 133.9 (CH), 147.1 (C), 153.7 (C), 158.0 (C), 162.2 (HC=N) ppm. MS (ESI- TOF) m/z: 263.24 (M$^+$+H).

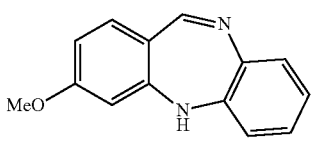

Compound 4

3-Methoxy-5H-dibenzo[b,e][1,4]diazepine: From N-(2-bromo-4-methoxybenzylidene)-4-methylbenzenesulfonamide (0.50 g, 1.4 mmol) and 2-bromoaniline (0.241 g), according to the general procedure the title compound was obtained as a brown solid/oil (0.218 g, 75%). $^1$H NMR (400 MHz, CDCl$_3$): δ 3.87 (s, 3H, OMe), 6.95-7.08 (m, 3H, ArH), 7.31-7.35 (m, 1H, ArH), 7.62-7.64 (m, 1H, ArH), 7.89-7.91 (m, 1H, ArH), 8.27-8.29 (m, 1H, ArH), 8.66 (br s, 1H, HC=N) ppm. $^{13}$C NMR (100 MHz, CDCl$_3$): δ 55.9 (OMe), 114.6 (CH), 118.1 (CH), 120.0 (CH), 124.9 (CH), 126.8 (C), 128.5 (CH), 128.9 (C), 130.6 (CH), 131.0 (C), 132.6 (C), 133.2 (CH), 156.8 (C), 159.9 (HC=N) ppm. MS (ESI-TOF) m/z: 225.27 (M$^+$+H).

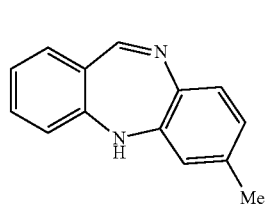

Compound 7

7-Methyl-5H-dibenzo[b,e][1,4]diazepine: From N-(2-bromobenzylidene)-4-methylbenzenesulfonamide (0.50 g, 1.5 mmol) and 2-bromo-5-methylaniline (0.279 g), according to the general procedure the title compound was obtained as a white oil (0.203 g, 65%). $^1$H NMR (400 MHz, CDCl$_3$): δ 2.36 (s, 3H, CH$_3$), 6.86-6.93 (m, 2H, ArH), 7.32-7.36 (m, 1H, ArH), 7.41-7.46 (m, 1H, ArH), 7.49.7.51 (m, 1H, ArH), 7.62-7.67 (m, 1H, ArH), 8.30-8.33 (m, 1H, ArH), 8.74 (br s, 1H, HC=N) ppm. MS (ESI- TOF) m/z: 209.27 (M$^+$+H).

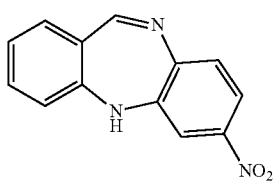

Compound 8

7-Nitro-5H-dibenzo[b,e][1,4]diazepine (4ad): From N-(2-bromobenzylidene)-4-methylbenzenesulfonamide (0.50 g, 1.5 mmol) and 2-bromo-5-nitroaniline (0.326 g), according to the general procedure the title compound was obtained as a yellow solid (0.215 g, 60%) m.p. 139.3-139.7° C. $^1$H NMR (400 MHz, CDCl$_3$): δ 7.40-7.46 (m, 2H, ArH), 7.67 (dd, J=1.2 and 8.0 Hz, 1H, ArH), 7.82 (d, J=8.8 Hz, ArH), 7.89 (d, J=2.8 Hz, ArH), 7.96 (dd, J=2.8 and 8.8 Hz, ArH), 8.31 (dd, J=1.2 and 8.0 Hz, ArH), 8.82 (br s, 1H, HC=N) ppm. $^{13}$C NMR (100 MHz, CDCl$_3$): δ 114.6 (CH), 121.3 (CH), 126.0 (C), 126.8 (C), 128.1 (CH), 129.8 (CH), 133.6 (CH), 133.7 (C), 133.8 (CH), 133.9 (CH), 148.1 (C), 151.5 (C), 162.8 (HC=N) ppm. MS (ESI- TOF) m/z: 240.23 (M$^+$+H).

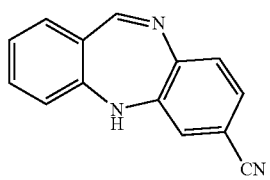

Compound 9

5H-dibenzo[b,e][1,4]diazepine-7-carbonitrile: From N-(2-bromobenzylidene)-4-methylbenzenesulfonamide (0.25 g, 0.74 mmol) and 3-amino-4-bromobenzonitrile (0.146 g), according to the general procedure, the title compound was obtained as a yellow semi-solid (0.085 g, 53%). $^1$H NMR (400 MHz, CDCl$_3$): δ 3.68 (br s, 1H, NH), 7.11 (d, J=8.0 Hz, ArH), 7.38-7.48 (m, 2H, ArH), 7.63-7.67 (m, 2H, ArH), 7.93 (d, J=1.6 Hz, ArH), 8.29 (dd, J=2.0 and 7.8 Hz, ArH), 8.74 (br s, 1H, HC=N) ppm. $^{13}$C NMR (100 MHz, CDCl$_3$): δ 110.5 (C), 117.7 (C), 118.3 (C), 120.6 (CH), 126.7 (C), 128.1 (CH), 129.8 (CH), 132.5 (CH), 133.6 (CH), 133.7 (C), 133.8 (CH), 136.6 (CH), 154.7 (C), 162.5 (HC=N) ppm.

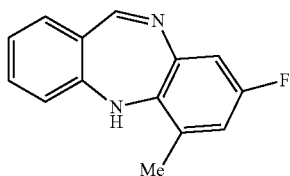

Compound 10

8-Fluoro-6-methyl-5H-dibenzo[b,e][1,4]diazepine: From N-(2-bromobenzylidene)-4-methylbenzenesulfonamide (0.50 g, 1.5 mmol) and 2-bromo-4-fluoro-6-methylaniline (0.304 g), according to the general procedure, the title compound was obtained as a yellow solid (0.251 g, 74%) m.p. 78.4-79.0° C. $^1$H NMR (400 MHz, CDCl$_3$): δ 2.22 (s, 3H, CH$_3$), 6.69-6.95 (m, 1H, ArH), 7.21-7.23 (m, 1H, ArH), 7.36-7.45 (m, 2H, ArH), 7.54-7.66 (m, 1H, ArH), 8.27-8.29 (m, 1H, ArH), 8.67 (br s, 1H, HC=N) ppm. $^{13}$C NMR (100 MHz, CDCl$_3$): δ 29.8 (CH$_3$), 116.6 (d, J=21.7 Hz, CH), 117.6 (d, J=24.9 Hz, CH), 126.2 (C), 128.0 (CH), 129.2 (CH), 131.5 (C), 133.1 (CH), 133.4 (CH), 134.3 (C), 138.5 (C), 146.5 (C), 159.0 (d, J=244.7 Hz, C—F), 165.1 (HC=N) ppm. MS (ESI- TOF) m/z: 227.26 (M$^+$+H).

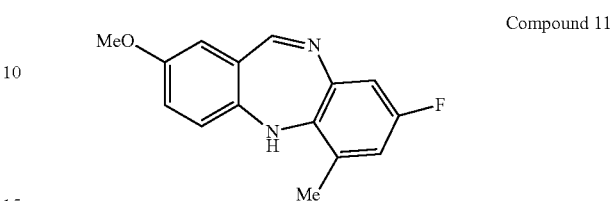

Compound 11

8-Fluoro-2-methoxy-6-methyl-5H-dibenzo[b,e][1,4]diazepine):
From N-(2-bromo-5-methoxybenzylidene)-4-methylbenzenesulfonamide (0.50 g, 1.4 mmol) and 2-bromo-4-fluoro-6-methylaniline (0.276 g), according to the general procedure the title compound was obtained as a yellow solid (0.216 g, 62%) 68.5-69.2° C. $^1$H NMR (400 MHz, CDCl$_3$): δ 2.22 (s, 3H, CH$_3$), 3.88 (s, 3H, OMe). 6.91.6.98 (m, 2H, ArH), 7.21-7.24 (m, 1H, ArH), 7.51-7.53 (m, 1H, ArH), 7.80-7.81 (m, 1H, ArH), 8.63 (br s, 1H, HC=N) ppm. $^{13}$C NMR (100 MHz, CDCl$_3$): δ 19.3 (CH$_3$), 55.9 (OMe), 112.4 (CH), 116.5 (d, J=21.7 Hz, CH), 117.1 (C), 117.4 (d, J=26.9 Hz, CH), 120.8 (CH), 123.4 (C), 131.5 (d, J=8.2 Hz, C), 134.1 (CH), 134.7 (d, J=3.1 Hz, C), 146.4 (C), 159.0 (d, J=244.6 Hz, C—F), 159.3 (C), 165.0 (HC=N) ppm. MS (ESI- TOF) m/z: 257.28 (M$^+$+H).

Naturally, the present application is by no means restricted to the embodiments described in this document, and a person with average skills in the art might predict many possibilities of altering the same without departing from the general idea, as defined in the claims.

Accordingly, the scope of the present application is to be construed in accordance with the substance defined by the following claims.

Abbreviations
DBU 1,8-Diazabicyclo[5.4.0]undec-7-ene
DIPA Diisopropylamine
DMA Dimethylacetamide
NHC N-Heterocyclic Carbene
NMM N-Methylmorpholine
NMP N-Methylpiperidine
PEPPSI catalyst Pyridine-Enhanced Precatalyst Preparation Stabilization and Initiation
SPhos 2-Dicyclohexylphosphino-2',6'-dimethoxybiphenyl
TBAAc Tetrabutylammonium acetate
Tf Triflate (trifluoromethylsulfonyl)
TFA Trifluoroacetic acid
XantPhos 4,5-Bis(diphenylphosphino)-9,9-dimethylxanthene
XPhos 2-Dicyclohexylphosphino-2',4',6'-triisopropylbiphenyl

REFERENCES

A. J. Burke, C. S. Silva, Catalytic Areolation Methods From the Academic Lab to the Industrial Process, Wiley-VCH, 2015, Weinheim.
R. D. Charan, G. Schlingmann, J. Janso, V. Bernan, X. Feng, G. T. Carter, J. Nat. Prod. 2004, 67, 1431.
X. Diao, L. Xu, W. Zhu, Y. Jiang, H. Wang, Y. Guo, D. Ma, Org. Lett. 2011, 13, 6422.

A. S. Guram, R. A. Rennels, S. L. Buchwald, *Angew. Chem. Int. Ed.* 1995, 34, 1348.
J. F. Hartwig, in Modern Amination Methods, A. Ricci (Ed.) pp 195, Wiley-VCH, Weinheim, 2000.
J. Louie, J. F. Hartwig, *Tetrahedron Lett.* 1995, 36, 3609.
F. Hunziker, F. Kunzle, J. Schmutz, O. Schindler, *Helv. Chim. Acta* 1964, 47, 1163.
D. Lednicer, Strategies for Organic Drug Synthesis and Design, John Wiley & Sons Inc., New York 1998.
X. Li, L. Yang, X. Zhang, D. Zhang-Negrerie, Y. Du, K. Zhao, *J. Org. Chem.* 2014, 79, 955.
R. J. Lundgren, M. Stradiotto, *Chem. Eur. J.* 2012, 18, 9758.
D. Peixoto, A. Locati, C. S. Marques, A. Goth, J. P. Prates Ramalho, A. J. Burke, *RSC Advances.* 2015, 5, 99990-99999.
S. M. Weinreb, *Top. Curr. Chem.* 1997, 190, 131.
M. Yazdanian, S. L. Glynn, J. L. Wright, A. Hawi. *Pharm. Res.* 1998, 15, 1490.

The invention claimed is:

1. A process for the catalytic one-pot synthesis of products of formula (III) from substrates of formula (I) and (II) respectively,

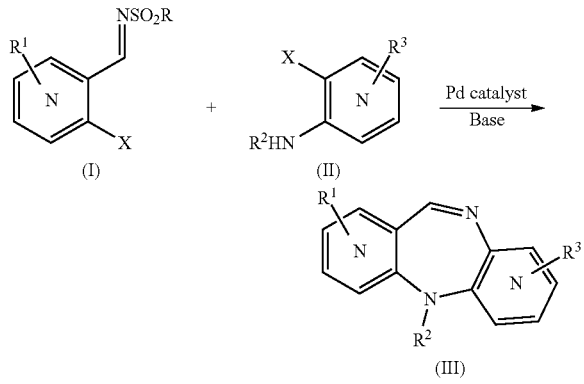

wherein,
X represents a halogen group or a triflate group (OTf);
R represents, an alkyl or aryl group;
$R^1$ and $R^3$ represent a hydrogen, a saturated alkyl, allyl, vinyl or cycloalkyl group, or an aryl group, or an OH, tiol, amino, nitro, cyano, aldehyde, ketone, ester, thioester, carboxylic acid, carbamate, ether or a thioeter group;
$R^2$ represents a hydrogen, an alkyl, allyl, vinyl or aryl group;
comprising the use of an active palladium catalyst, at a loading of between 0.1 and 5 mol %, wherein the reaction is
conducted by adding a palladium complex, a ligand at a loading of between 0.25 and 10 mol %, and a base in a solvent.

2. The process according to claim 1, wherein the active catalyst is prepared by adding the ligand to the palladium complex in a dry solvent, under an inert atmosphere and allowing the mixture to stir up to 24 h with a temperature range from 50 to 130° C.

3. The process according to claim 1, wherein the palladium complex used is selected from the group consisting of $Pd(OAc)_2$, PEPPSI-iPr catalyst, $Pd_2(dba)_3 \cdot CHCl_3$, [Pd(TFA)$_2$], $PdCl_2(dppf)$, $Pd(PPh_3)_4$, cationic palladium (II) complexes and Pd—NHCs.

4. The process according to claim 1, wherein the reaction solvent used is selected from the group consisting of: toluene, dimethyl ether, diethyl ether, 1,4-dioxane, acetonitrile, chloroform, DMF, DMA and NMP.

5. The process according to claim 1, wherein the ligand is a monophosphane type ligand.

6. The process according to claim 1, wherein the base is selected from the group consisting of triethylamine, $K_2CO_3$, $Na_2CO_3$, $CaCO_3$, $Ba(OH)_2$, KOAc, DIPA, $K_3PO_4$, NMM, DBU, KOH, KF, $Cs_2CO_3$, and KOtBu.

7. The process according to claim 1, wherein the substrate of formula (I) is pre-formed or formed in situ.

8. The process according to claim 1, wherein the reaction is run under an inert atmosphere.

9. The process according to claim 1, wherein the reaction temperature ranges between 50 and 130° C.

10. The process according to claim 1, wherein the halogen group is selected from the group consisting of Br, Cl and I.

* * * * *